United States Patent [19]

Garland

[11] Patent Number: 4,496,485

[45] Date of Patent: Jan. 29, 1985

[54] ASYMMETRIC 7-O-(SUBSTITUTED ACETYL)-4-DEMETHOXYDAUNOMYCI-NONES

[75] Inventor: Robert B. Garland, Northbrook, Ill.

[73] Assignee: G. D. Searle & Co., Skokie, Ill.

[21] Appl. No.: 555,270

[22] Filed: Nov. 25, 1983

[51] Int. Cl.³ .............................................. C07C 50/27
[52] U.S. Cl. .................................. 260/351.1; 260/376
[58] Field of Search ............................. 260/351.1, 376

[56] References Cited

U.S. PATENT DOCUMENTS

| 4,046,878 | 9/1977 | Patelli et al. | 424/180 |
| 4,077,988 | 3/1978 | Arcamone et al. | 260/376 |
| 4,161,480 | 7/1979 | Garland et al. | 260/365 |

FOREIGN PATENT DOCUMENTS 1509875  6/1976  United Kingdom .

OTHER PUBLICATIONS

C. M. Wong et al., Synthetic Studies of Hydronaphthacenic Antibiotics, I. Synthesis of 4-Demethoxy-7-O-methyl Daunomycinone *Can. J. Chem.,* 49, 2712, (1971).

S. Terashima et al., Asymmetric Synthesis of Optically Active Anthracyclinones, *Tetrahedron Lett.,* 4937, (1978).

F. Arcamone et al., Synthesis and Antitumor Activity of 4-Demethoxydaunorubicin, 4-Demethoxy-7,-9-diepidaunorubicin, and Their B Anomers. *Cancer Treat. Rep.,* 60, 829, (1976).

*Primary Examiner*—Glennon H. Hollrah
*Assistant Examiner*—Raymond Covington
*Attorney, Agent, or Firm*—John J. McDonnell

[57] ABSTRACT

This invention relates to novel diastereomeric 7-O-(substituted acetyl)-4-demethoxydaunomycinones that are useful in the preparation of optically pure 4-demethoxydaunorubicin, a drug used in the treatment of certain cancers.

4 Claims, No Drawings

ASYMMETRIC 7-O-(SUBSTITUTED ACETYL)-4-DEMETHOXYDAUNOMYCINONES

BACKGROUND OF THE INVENTION (a) Field of the Invention

This invention relates to novel compounds, Formula I, that permit the unexpectedly efficient and convenient resolution of racemic 4-demethoxydaunomycinone, the anthracycline aglycone of the anti cancer drug 4-demethoxydaunorubicin. This compound is disclosed in U.S. Pat. No. 4,161,480.

Daunorubicin and doxorubicin are effective antineoplastic drugs, although cumulative cardiac toxicity limits the total quantity of these drugs that may be administered during a course of treatment. 4-Demethoxydaunorubicin is also an effective antineoplastic drug, reportedly more active in mice than daunorubicin against sarcoma 180 and against L1210 and Gross leukemias. F. Arcamone et al. Synthesis and Antitumor Activity of 4-Demethoxydaunorubicin, 4-Demethoxy-7,9-diepidaunorubicin, and Their β Anomers. Cancer Treat. Rep., 60, 829 (1976).

Although racemic 4-demethoxydaunomycinone may be prepared by several methods, not all isomers are equally active and some isomers are negligibly active. Since the glycoside moiety of daunosamine is difficult to prepare and thus expensive, a method of resolving the aglycone 4-demethoxydaunomycinone before coupling with daunosamine is desirable. The compounds of this invention provide a convenient means of completely resolving racemic 4-demethoxydaunomycinone. For example, reaction of racemic 4-demethoxydaunomycinone with readily available l-menthoxyacetyl chloride, followed by separation of diastereomers, affords the isomer of Formula II used ultimately to prepare the more active and preferred isomer of 4-demethoxydaunorubicin. Moreover, isomer II can be prepared without contamination by the undesired isomer, Formula III.

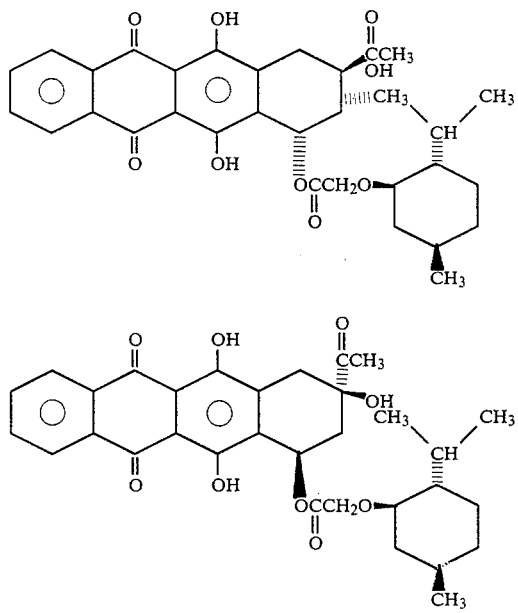

(b) Prior Art

Several methods have been described for the preparation of racemic 4-demethoxydaunomycinone, for example, C. M. Wong et al. Synthetic Studies of Hydronaphthacenic Antibiotics. I. The Synthesis of 4-Demethoxy-7-O-methyl Daunomycinone. Can. J. Chem., 49, 2712 (1971); U.S. Pat. No. 4,161,480.

Various resolution methods for 4-demethoxydaunorubicin or its precursors are known but are typically less convenient and efficient than the simple resolution using the compounds of this invention. Some methods rely on the separation of diastereomeric isomers formed upon reaction with the optically active glycoside daunosamine, for example, British Pat. No. 1,509,875 and U.S. Pat. No. 4,046,878, but these methods allow incorporation of only half of the expensive daunosamine in the preferred 4-demethoxydaunorubicin isomer.

Other methods form an optically active derivative at an intermediate step, with subsequent separation of isomers at some later step, but these methods are typically quite complex. See, e.g., S. Terashima et al. Asymmetric Synthesis of Optically Active Anthracyclinones. Tetrahedron Lett., 4937 (1978) (asymmetric "bromolactonization").

Other methods form an optically active precursor at an early step, with subsequent resolution of diastereomers required by later introduction of the asymmetric center at the 9-position—see (1) U.S. Pat. No. 4,077,988; (2) F. Arcamone et al. Synthesis and Antitumor Activity of 4-Demethoxydaunorubicin, 4-Demethoxy-7,9-diepidaunorubicin, and Their β Anomers. Cancer Treat. Rep., 60, 829 (1976)—but such methods present the possibility of later racemization at the 7-position.

SUMMARY OF THE INVENTION

The following resolved diastereomeric 7-O-(1-menthoxy-acetyl)-4-demethoxydaunomycinones have been discovered to be novel and useful intermediates in the preparation of 4-demethoxydaunorubicin, a drug useful in the treatment of certain cancers. Since this invention employs a reaction of racemic 4-demethoxydaunomycinone (which may be prepared by several methods that avoid the need for early optical resolution) with readily available 1-menthoxyacetyl chloride, and since this invention does not require the use of expensive daunosamine until after the resolution step, the compounds of this invention provide an effective and convenient improvement in the preparation of optically pure 4-demethoxydaunorubicin.

This invention relates to compounds of Formula I:

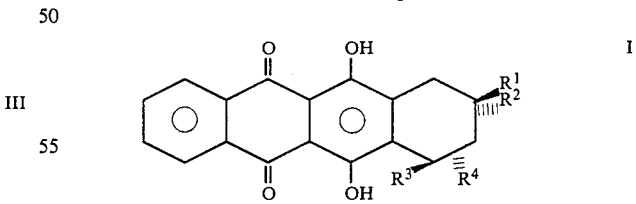

wherein one of $R^1$ or $R^2$ is acetyl and the other is hydroxy;
wherein one of $R^3$ or $R^4$ is hydrogen and the other is $O(CO)CH_2OR^5$;
wherein the hydroxy and the $O(CO)CH_2OR^5$ are in a cis relationship;
wherein $R^5$ is an asymmetric radical such as:
l-menthyl, d-menthyl, l-isomenthyl, d-isomenthyl, d-neomenthyl, bornyl, l-isopinocamphyl with l-menthyl being preferred.

DESCRIPTION OF THE INVENTION

The compounds of this invention are prepared by the following general methods, illustrated by the following Scheme.

SCHEME

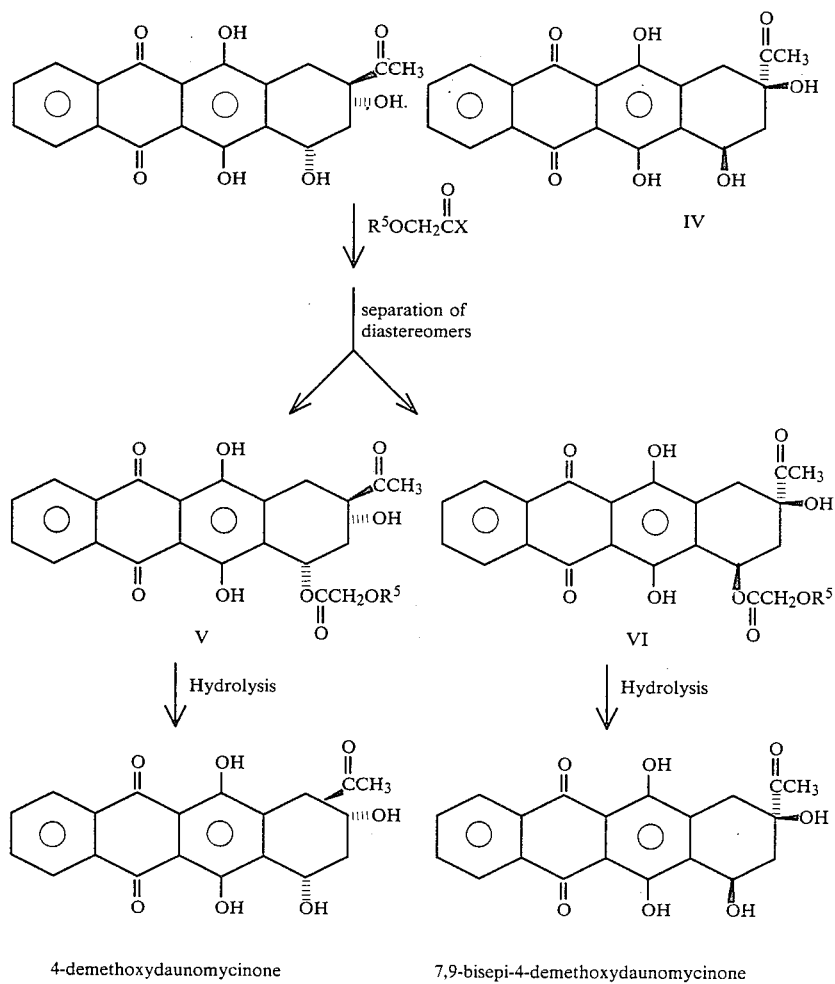

4-demethoxydaunomycinone     7,9-bisepi-4-demethoxydaunomycinone

Racemic 4-demethoxydaunomycinone, represented by Formula IV, reacts with an optically active acylating agent, preferably l-menthoxyacetyl chloride, in a suitably unreactive organic solvent. In preparing the preferred l-menthoxyacetate esters of this invention, preferred acylating conditions include anhydrous toluene at about 100° C. The crude reaction product subsequently obtained includes a diastereomeric mixture of l-menthoxyacetate esters, Formulas V and VI. A preliminary chromatographic separation on silica gel is typically employed to separate these esters V and VI from unreacted 4-demethoxydaunomycinone. Using the preferred eluent dichloromethane-ethyl acetate, pure isomer V elutes first, followed by isomer VI. Some early fractions of isomer VI are contaminated by isomer V, but may be purified by crystallization—for example, using toluene, a 1:1 mixture of V and VI crystallizes, leaving virtually pure isomer VI in solution. Isomer VI may be isolated from that solution, and the 1:1 mixture may again be chromatographed. Each of V and VI is finally purified by crystallization. A preferred recrystallization solvent is toluene.

Each of isomers V and VI may be converted to the respective resolved isomers of 4-demethoxydaunomycinone by acid hydrolysis. A preferred method employs extended reflux in tetrahydrofuran containing 10% aqueous hydrochloric acid, followed by dilution with water and subsequent crystallization. An optional chromatographic purification of the crystallization liquors affords more of the same isomer and trace quantities of other epimers. Thus, isomer V affords pure 4-demethoxydaunomycinone and isomer VI affords pure 7,9-bisepi-4-demethoxydaunomycinone (ent-4-demethoxydaunomycinone).

The preferred embodiments of this invention include the l-menthyloxyacetate esters of Formulas II and III. The most preferred embodiment is the l-menthyloxyacetate ester of Formula II.

The following examples further illustrate details for the preparation of the compounds of this invention and subsequent conversion to resolved isomers of 4-demethoxydaunomycinone. The invention, which is set forth in the foregoing disclosure, is not to be construed or limited in spirit or in scope by these examples. Those skilled in the art will readily understand that known variations of the conditions and processes of the following preparative procedures can be used to prepare these compounds. All temperatures are degrees celsius unless otherwise noted.

DESCRIPTION OF THE PREFERRED EMBODIMENTS

EXAMPLE 1

Mixture of 7-O-(1-menthoxyacetyl)-4-demethoxydaunomycinone and 7,9-bisepi-7-O-(1-menthoxyacetyl)-4-demethoxydaunomycinone A solution of 7.48 g of racemic 4-demethoxydaunomycinone in 400 ml of toluene was dried by azeotroping and then stirred with 6.26 g of 1-menthoxyacetyl chloride for 18 hours at 100°. Cooling the mixture and collecting the resultant precipitate afforded 5.74 g of the title mixture. The filtrate was washed with 5% aqueous sodium bicarbonate and then with water, dried over sodium sulfate, and concentrated to ca. 50 ml. Addition of diethyl ether produced an additional 2.71 g of the title mixture. A further 1.80 g of the title mixture was isolated by column chromatography on silica gel using dichloromethane-ethyl acetate as eluent. Total yield of the title mixture was 10.25 g.

EXAMPLE 2

7-O-(1-menthoxyacetyl)-4-demethoxydaunomycinone (SC-36474), Method A

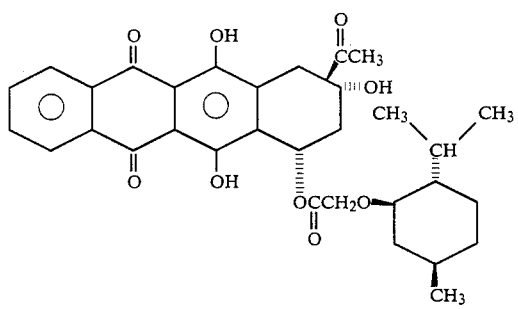

A portion (4.0 g) of the title mixture of Example 1 was purified using preparative liquid chromatography on silica gel. Elution with 92:8 dichloromethane-ethyl acetate afforded 1.60 g of the title compound. Recrystallization from toluene-hexane afforded 1.45 g of analytically pure title compound, m.p. 197°–198°. $[\alpha]_D -13.3°$ (0.1% CHCl$_3$)

Analysis. Calcd. for C$_{32}$H$_{36}$O$_9$: C, 68.07, H, 6.43.
Found: C, 67.98; H, 6.38.

EXAMPLE 3

7,9-bisepi-7-O-(1-menthoxyacetyl)-4-demethoxydaunomycinone (SC-36475), Method A

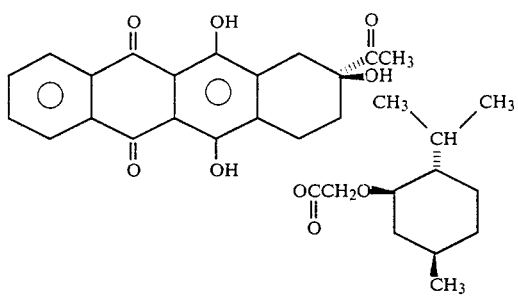

Later chromatographic fractions of Example 2, after removing solvent, were dissolving in 100 ml of toluene and allowed to stand for at least 24 hours. A 1:1 mixture of diastereomers, m.p. 189°–190°, (see Example 1) precipitated and was set aside for chromatographic recycling. The filtrate afforded 1.55 g of a solid which was purified by recrystallization from toluene-hexane, giving 1.48 g of pure title compound, m.p. 192°–193°. $[\alpha]_D -62.2°$ (0.1% CHCl$_3$)

Analysis. Calcd. for C$_{32}$H$_{36}$O$_9$: C, 68.07; H, 6.43.
Found: C, 68.13; H, 6.40.

Further elution with 4:1 dichloromethane-ethyl acetate afforded racemic 4-demethoxydaunomycinone, which could be recycled as in Example 1.

EXAMPLE 4

7-O-(1-menthoxyacetyl)-4-demethoxydaunomycinone, Method B

The title compound (2.85 g) was also isolated from the product mixture of Example 1 (8.0 g) by low-pressure chromatography on neutral silicic acid (200–325 mesh) using 95:5 dichloromethane-ethyl acetate. The crystalline solid was indistinguishable from the title compound of Example 2.

EXAMPLE 5

7,9-bisepi-7-O-(1-menthoxyacetyl)-4-demethoxydaunomycinone, Method B

The title compound (2.78 g) was isolated from later chromatographic fractions of Example 4. The crystalline solid was indistinguishable from the title compound of Example 3.

Further elution with 4:1 dichloromethane-ethyl acetate afforded racemic 4-demethoxydaunomycinone, which could be recycled as in Example 1.

EXAMPLE 6

4-demethoxydaunomycinone

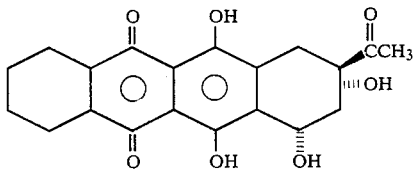

A solution of 4.00 g of the title compound of Example 2 (or Example 4) in 200 ml of tetrahydrofuran containing 120 ml of 10% aqueous hydrochloric acid was heated at reflux. After four days ca. 50 ml was distilled away, and the mixture was diluted with 100 ml of water and allowed to cool. The resultant solid was collected, washed well with water, and air dried. Recrystallization from dichloromethane-diethyl ether afforded 2.15 g of the title compound, m.p. 185°–186°. $[\alpha]_D +177°$ (0.1% dioxane)

An additional 0.2 g of the title compound was isolated from the aqueous filtrate (after extraction into dichloromethane) and the dichloromethane-diethyl ether filtrate by chromatography on silicic acid (4:1 toluene-ethyl acetate eluent). Later fractions afforded traces of 7-epi-4-demethoxydanomycinone, m.p. 213°–215°, $[\alpha]_D -78°$ (0.1% dioxane).

EXAMPLE 7

7,9-bisepi-4-demethoxydaunomycinone

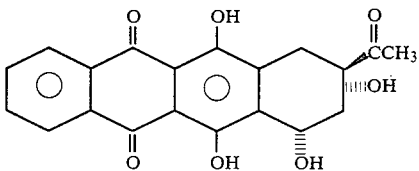

The title compound (2.34 g), m.p. 185°–186°, was prepared from the title compound of Example 3 (or Example 5) using the method of Example 6. $[\alpha]_D -171°$ (0.1% dioxane)

Later chromatographic fractions afforded traces of 9-epi-4-demethoxydanomycinone, m.p. 212°–214°, $[\alpha]_D +77°$ (0.1% dioxane).

What is claimed is:

1. A compound of the formula:

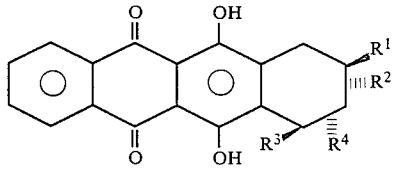

wherein one of $R^1$ or $R^2$ is acetyl and the other is hydroxy;

wherein one of $R^3$ and $R^4$ is hydrogen and the other is $O(CO)CH_2OR^5$;

wherein the hydroxy and the $O(CO)CH_2OR^5$ are in a cis relationship; and wherein $R^5$ is an asymmetric radical selected from the group consisting of l-menthyl, d-menthyl, l-isomenthyl, d-isomenthyl, d-neomenthyl, bornyl and l-isopinocamphyl.

2. A compound according to claim 1 wherein $R^5$ is l-menthyl.

3. A compound according to claim 2 having the formula:

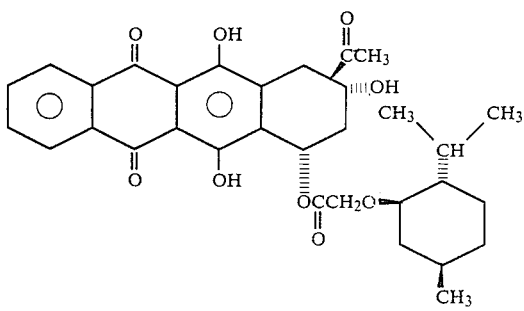

4. A compound according to claim 2 having the formula:

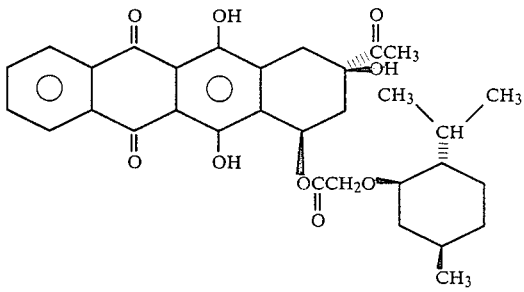

* * * * *